US00PP14572P29

(12) United States Plant Patent
Heims

(10) Patent No.: US PP14,572 P2
(45) Date of Patent: Mar. 2, 2004

(54) EUPHORBIA PLANT NAMED 'BLUE LAGOON'

(50) Latin Name: *Euphorbia amygdaloides var. robbiae×Europhorbia characias*
Varietal Denomination: Blue Lagoon

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 22 days.

(21) Appl. No.: 10/345,686

(22) Filed: Jan. 15, 2003

(51) Int. Cl.[7] ..... A01H 5/00
(52) U.S. Cl. ..... Plt./302
(58) Field of Search ..... Plt./302

*Primary Examiner*—Bruce R. Campell
*Assistant Examiner*—Louanne Krawczewicz Myers
(74) *Attorney, Agent, or Firm*—Klarquist Sparkman, LLP

(57) ABSTRACT

A new and distinct hybrid of Euphorbia plant characterized by blue green leaves and a rhizomatous habit. The upright stems flower in their second year with a bright chartreuse inflorescence, which then fades to orange and red tones.

2 Drawing Sheets

Botanical classification: *Euphorbia amygdaloides* var. *robbiae×Euphoriba characias.*
Variety denomination: 'Blue Lagoon'.

BACKGROUND OF THE INVENTION

The present invention relates to a new and distinct cultivar of a hardy, suffrutescent perennial of the genus Euphorbia, known by the cultivar name of 'Blue Lagoon'. The genus Euphorbia is a member of the family Euphorbiaceae.

The new cultivar originated as a garden cross between *Euphorbia amygdaloides* var. *robbiae* (seed parent, unpatented) and *Euphorbia characias* (pollen parent, unpatented). The cross was discovered when growing out the seedlings of *Euphorbia amygdaloides* var. *robbiae. Euphorbia characias* was the only other Euphorbia species in bloom and the seedling has the characteristics of both parents.

SUMMARY OF THE INVENTION

This new cultivar is characterized by:

1) Persistent winter foliage like the seed parent *Euphorbia amygdaloides* var. *robbiae.*
2) Blue green foliage.
3) Large plant size like the pollen parent *Euphorbia characias.*
4) Tall, chartreuse colored inflorescences.
5) Bract colors past maturity are orange and russet extending the showiness of the bloom time.
6) Habit is a basal clump which spreads by underground rhizomes like the seed parent.
7) Sterile, so no seed or unwanted seedlings are produced.
8) Not susceptible to winter wet which causes rot in many Euphorbia species.
9) Excellent vigor, rapid growth.

Asexual propagation by tissue culture using standard micropropagation techniques with terminal shoots as done in Canby, Oreg., shows that the foregoing characteristics and distinctions come true to form and are established and transmitted through succeeding propagations. This new cultivar has been reproduced only by asexual propagation (division and tissue culture). Each of the progeny exhibits identical characteristics to the original plant. The present invention has not been evaluated under all possible environmental conditions. The phenotype may vary with variations in environment without a change in the genotype of the plant.

DETAILED PLANT DESCRIPTION

Figure 1:
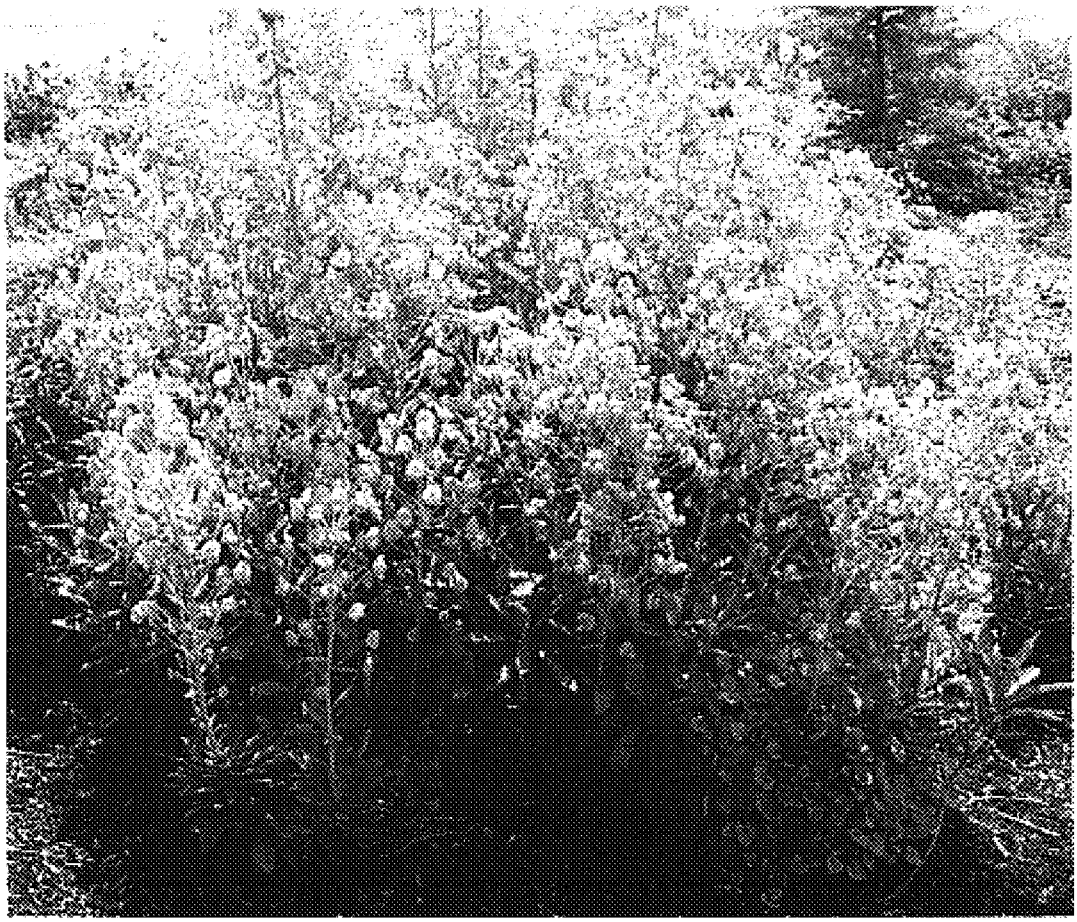
FIG. 1 shows a three-year-old Euphorbia 'Blue Lagoon' growing in the ground in a garden in June in Canby, Oreg.
Figure 2:
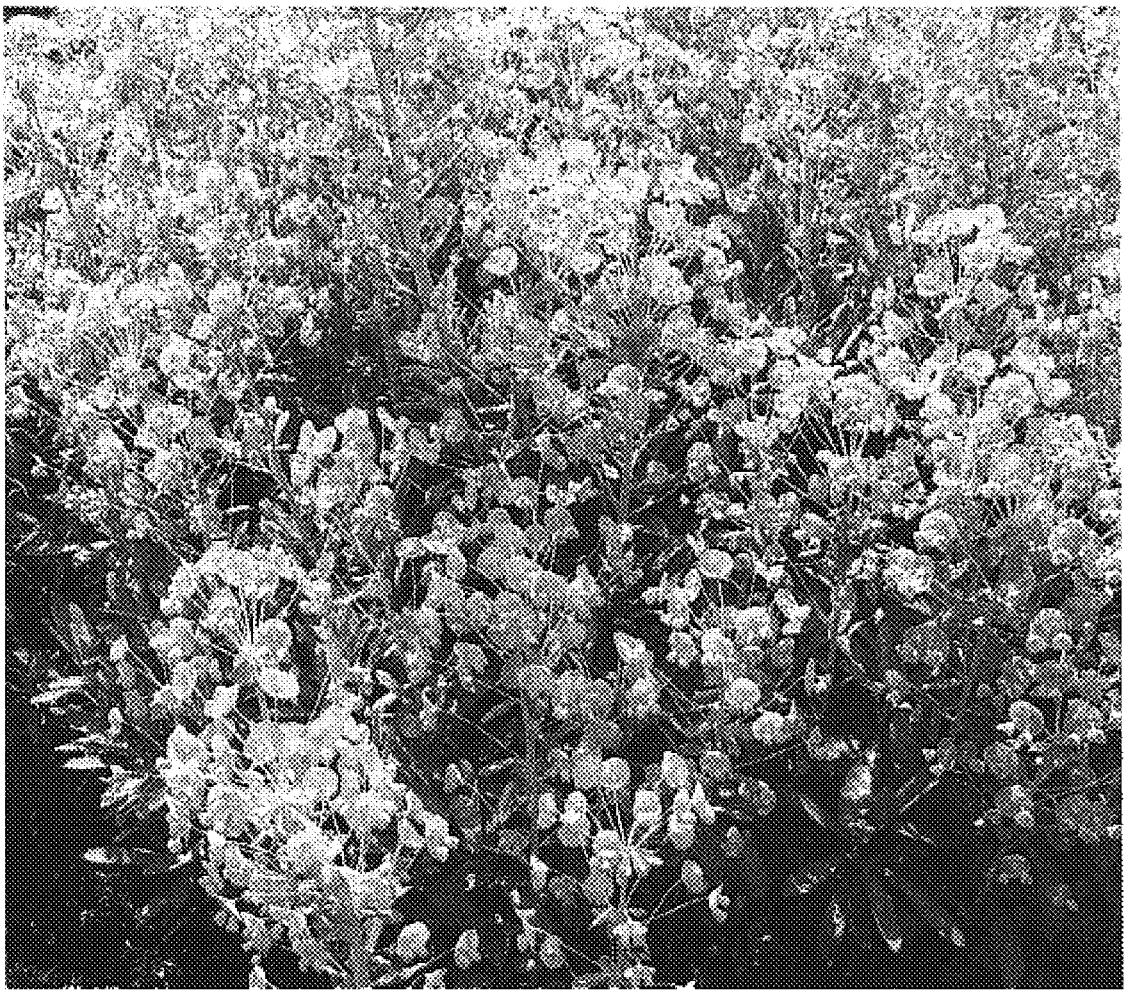
FIG 2 shows a close up of the same plant.

The following is a detailed description of the new Euphorbia hybrid based on observations of three-year-old specimens grown in the garden in Canby, Oreg. The color descriptions are all based on The Royal Horticultural Society Colour Chart.

Botanical name: *Euphorbia amygdaloides* var. *robbiae× Euphorbia characias.*
Cultivar name: 'Blue Lagoon'.
Plant:
- *Form.*—Upright, clumping.
- *Hardiness.*—USDA Zone 7 to 9.
- *Size.*—40 to 80 cm tall and 115 cm wide.
- *Habit.*—Suffrutescent and rhizomatous.

Stem:
- *Type.*—Upright, unbranched, tufted stems which are leafy only the first year and flowering the second year.
- *Size.*—3 to 6 mm wide and 30 to 72 cm tall.
- *Internodes.*—Variable, from 0.2 to 1 cm in the top 18 cm, becoming closer toward the top. Widely spaced on the lower part, from 2.5 to 8 cm.
- *Surface.*—Sparsely pubescent.
- *Color.*—Yellow Green 144A except at the base where it is Greyed Orange 174B.

Leaf:
- *Type.*—Simple.
- *Arrangement.*—Rosette or alternate.

*Shape.*—Oblanceolate.
*Venation.*—Pinnate.
*Margins.*—Entire.
*Apex.*—Acute, mucronulate.
*Base.*—Attenuate.
*Blade size.*—4.5 to 12.5 cm long and 1.7 to 2.4 cm wide.
*Vestiture.*—Glaucous above, sparsely pubescent below.
*Aspect.*—Matte.
*Texture.*—Leathery.
*Petiole length.*—0.7 to 1.4 cm.
*Petiole color.*—Yellow Green 144A.
*Leaf color.*—Blue green, between Green 137A and 139A with a glaucous bloom, Greyed Green 189A.
*Bottom side.*—Closest to Green 138B.

Inflorescence:
*Type.*—Terminal cyme.
*Number of involucre branches.*—20 to 200 per cyme.
*Involucre basal bracts.*—One per involucre, leaf-like, alternate, entire with attenuate bases, narrowly oblong (3.5 cm long and 6 mm wide)with a acute tip on lower involucres and obovate (2 cm long and 1 cm wide) with an obtuse tip on top involucres.
*Peduncle.*—Height — 28 cm on edges of clump to 90 cm in middle of the clump. Diameter — 0.4 to 0.7 cm. Color — Yellow Green 144B. Texture — Tomentose.
*Pedicel.*—Length — 2.5 to 10 cm. Texture — Sparsely tomentose. Color — Yellow Green 144B.
*Bloom period.*—April to July in Canby, Oreg.

*Flower bracts/involucres (the showy part of the flower):*
*Size.*—1 to 2 cm wide and 4 mm deep.
*Number of flower bracts per involucre branch.*—1 to 21.
*Description.*—Orbicular, two lobed.
*Color.*—Chartreuse, Yellow Green 154B. Past maturity the color changes to a duller chartreuse and orange shades, Yellow Green 151A with Greyed Orange 165C highlights, then changes to red shades, Greyed Red 182A and 184C.

Fragrance: None.
Cyathia: Pubescent, Yellow Green 154B.
Fruit: None formed. The plant is sterile, no viable fruit is formed.
Seed: None.
Disease problems: None observed. *Euphorbia amygdaloides* has problems with mildew and most Euphorbia have problems with root rot (if grown in heavy, wet soils). No mildew has been observed in 4 years on the mother plant of the new variety. No root rot problems have been observed.
Pest problems: No pest problems have been observed outdoors with spider mites or mealy bugs, the most likely problems.

COMPARISONS TO SIMILAR EUPHORBIA

Compared to its seed parent, *Euphorbia amygdaloides* var. *robbiae,* Euphorbia 'Blue Lagoon' is larger in size, blue green rather than deep green leaves, and much more colorful flowers. They both keep their foliage over the winter and spread by rhizomes.

Compared to its pollen parent, *Euphorbia characias*, Euphorbia 'Blue Lagoon' has a smaller, denser habit with blue green leaves rather hand grey green. The flowers of this new cultivar are more colorful, changing from chartreuse to orange to reds while *Euphorbia characias* is only chartreuse. In addition this new cultivar rhizomatomatous and does not have the problem of rotting over the winter due to winter wet.

Since the new cultivar is sterile, it doesn't spread by seed like its parents.

I claim:

1. A new and distinct hybrid of Euphorbia plant substantially as shown and described.

* * * * *